United States Patent [19]

Schenk

[11] Patent Number: 5,573,892
[45] Date of Patent: Nov. 12, 1996

[54] USE OF YELLOW COUPLERS OF THE INDOLO [3,2-B] GUINOLINE TYPE IN A COLOUR PHOTOGRAPHIC DEVELOPMENT PROCESS

[75] Inventor: Günther Schenk, Bergisch Gladbach, Germany

[73] Assignee: AGFA-Gevaert AG, Germany

[21] Appl. No.: 547,771

[22] Filed: Oct. 25, 1995

[30] Foreign Application Priority Data

Nov. 4, 1994 [DE] Germany .................. 44 39 329.6

[51] Int. Cl.⁶ .................................................. G03C 7/46
[52] U.S. Cl. .................... 430/388; 430/389; 430/383; 430/558; 430/502
[58] Field of Search .............................. 430/388, 389, 430/383, 558, 502

[56] References Cited

U.S. PATENT DOCUMENTS

| | | | |
|---|---|---|---|
| 2,186,045 | 1/1940 | Schneider | 430/558 |
| 2,886,436 | 5/1959 | Schmidt et al. | 430/558 |
| 3,171,740 | 3/1965 | Menzel et al. | 430/558 |
| 3,304,182 | 2/1967 | Froehuch | 430/558 |

FOREIGN PATENT DOCUMENTS 376166 7/1990 European Pat. Off. .

*Primary Examiner*—Geraldine Letscher
*Attorney, Agent, or Firm*—Connolly & Hutz

[57] ABSTRACT

Compounds of the formula I are suitable as photographic yellow couplers

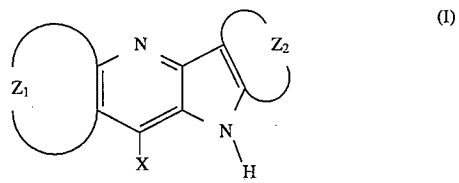

In formula I, $Z_1$, $Z_2$ mean residues to complete 5-, 6- or 7-membered rings of an aromatic or heteroaromatic nature; these rings may be substituted with substituents $R^1$, $R^2$, $R^3$ and $R^4$;

X means H or a substituent which is released under chromogenic development conditions.

10 Claims, No Drawings

USE OF YELLOW COUPLERS OF THE INDOLO [3,2-B] GUINOLINE TYPE IN A COLOUR PHOTOGRAPHIC DEVELOPMENT PROCESS

This invention relates to novel photographic colour couplers from which yellow image dyes may be formed on colour development, and to a corresponding photographic colour development process. The invention also relates to a colour photographic recording material which contains at lease one such colour coupler. The colour couplers used according to the invention are compounds of the following general formula I

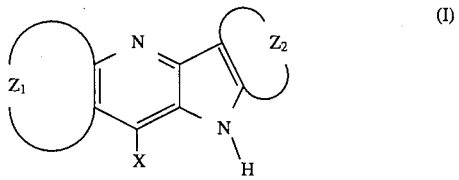

in which:
$Z_1$, $Z_2$ mean residues to complete 5-, 6- or 7-membered rings of an aromatic or heteroaromatic nature; these rings may be substituted with substituents $R^1$, $R^2$, $R^3$ and R4;
X means H or a substituent which is released under chromogenic development conditions.

It is known to produce colour photographic images by chromogenic development, i.e. by developing silver halide emulsion layers which have been exposed in accordance with an image by means of suitable chromogenic developer substances, known as colour developers, in the presence of suitable colour couplers, wherein the oxidation product of the developer substances, which is formed congruently with the silver image, reacts with the colour coupler forming a dye image. Aromatic compounds containing primary amino groups, particularly those of the p-phenylenediamine type, are usually used as colour developers.

A series of practical requirements is placed upon the colour couplers and the dyes obtained therefrom by chromogenic development. Thus, the raze of coupling of the colour couplers with the colour developer oxidation product should be as high as possible. The colour couplers, and the dyes obtained therefrom, must have sufficient resistance to light, elevated temperature and moisture. This applies both to fresh material and to processed material. For example, any coupler remaining in the image whites of the processed material must not yellow. Moreover, the dyes should be sufficiently resistant to gaseous oxidising and reducing agents. They must moreover be non-diffusibly immobilised and, on chromogenic development, should precipitate as the finest possible grain. Finally, the dyes arising from the colour couplers on chromogenic development must have a favourable absorption curve with a maximum corresponding to the particular desired partial image and the least possible secondary absorption. Thus, a yellow dye should ideally absorb blue light and largely transmit green and red light. Moreover, the absorption maxima of the dyes both in colour reversal and colour negative films should as far as possible correspond with the sensitising maxima of the colour paper materials used, for copying.

In addition to the novel colour couplers of the formula I, the present invention also provides a photographic colour development process in which a colour photographic recording material having at least one silver halide emulsion layer exposed in accordance with an image is developed in the presence of a colour coupler compound and a colour developer compound, characterised in that the colour coupler compound is of the following formula (I):

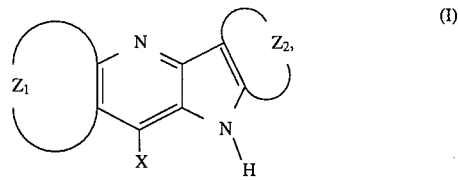

in which:
$Z_1$, $Z_2$ mean residues to complete 5-, 6- or 7-membered rings of an aromatic or heteroaromatic nature; these rings may be substituted with substituents $R^1$, $R^2$, $R^3$ and $R^4$;
X means H or a substituent which is released under chromogenic development conditions.

The present invention also provides a colour photographic recording material which contains a colour coupler of the formula I.

The colour couplers according to the invention are preferably compounds of the formula II

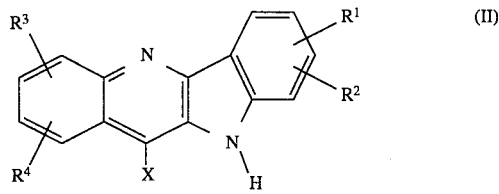

in which:
$R^1$, $R^2$, $R^3$, $R^4$ mean an H atom or a substituent;
x means an H atom or a residue which is released under chromogenic development conditions.

$R^1$, $R^2$, $R^3$, $R^4$ but at least one of these substituents, may act to ballast the coupler.

The substituents $R^1$, $R^2$, $R^3$ and $R^4$ are not specifically restricted, typical examples are, far example, halogen, alkyl, cycloalkyl, aryl, anilino, acylamino, sulphonamido, alkylthio, arylthio, alkenyl, together with cycloalkenyl, alkynyl, heterocyclyl, sulphony, sulphinyl, phosphonyl, acyl, carbamoyl, sulphamoyl, cyano, alkoxy, sulphonyloxy, aryloxy, heterocyclyloxy, siloxy, acyloxy, carbamoyloxy, amino, alkylamino, imido, ureido, suiphamoylamino, alkoxycarbonylamino, aryioxycarbonyiamino, alkoxycarbonyl, aryloxycarbonyl, heterocyclylthio, thioureido, carboxy, nitro, sulphonate etc. spiro substituents and bridged hydrocarbon residues.

Alkyl substituents for $R^1$, $R^2$, $R^3$ or $R^4$ are here preferably residues having 1 to 32 C atoms, linear or branched, unsubstituted or substituted, for example substituted with alkoxy, aryloxy or acyl.

Aryl substituents for $R^1$, $R^2$, $R^3$ or $R^4$ are here preferably phenyl or substituted phenyl residues.

Acylamino substituents for $R^1$, $R^2$, $R^3$ or $R^4$ are here preferably alkylcarbonylamino, arylcarbonylamino, hetarylcarbonylamino, ureido.

Sulphonamido substituents for $R^1$, $R^2$, $R^3$ or $R^4$ are here preferably alkylsulphonylamino, arylsulphonylamino, heteraylsulphonylamino.

The alkyl and aryl fragments in the alkylthio and arylthio substituents for $R^1$, $R^2$, $R^3$ or $R^4$ have an identical range of meaning to that stated for the alkyl and aryl substituents $R^1$, $R^2$, $R^3$ or $R^4$.

Alkeny substituents for $R^1$, $R^2$ $R^3$ or $R^4$ contain 2 to 32 carbon atoms; the alkenyl substituent may be linear or branched.

Cycloalkyl and cyloalkenyl substituents for $R^1$, $R^2$, $R^3$ or $R^4$ contain 3 to 12 C atoms, preferably 5 to 7 C atoms.

Sulphony substituents for $R^1$, $R^2$, $R^3$ or $R^4$ are for example, any type of alkylsulphonyl, arylsulphonyl or hetarylsulphonyl.

Sulphinyl substituents for $R^1$, $R^2$, $R^3$ or $R^4$ are, for example, any type of alkylsulphinyl, arylsulphinyl or hetarylsulphinyl.

Phosphonyl substituents for $R^1$, $R^2$, $R^3$ or $R^4$ are for example, any type of alkylphosphonyl, alkoxyphosphonyl, aryloxyphosphonyl or arylphosphonyl. Acyl substituents for $R^1$, $R^2$, $R^3$ or $R^4$ are, for example any type of alkylcarbonyl or arylcarbonyl.

Carbamoyl substituents for $R^1$, $R^2$, $R^3$ or $R^4$ are for example, any type of alkylcarbamoyl, arylcarbamoyl or hetarylcarbamoyl.

Sulphamoyl substituents for $R^1$, $R^2$, $R^3$ or $R^4$ are, for example, any type of alkylsulphamoyl, arylsulphamoyl or hetarylsulphamoyl.

Acyloxy substituents for $R^1$, $R^2$, $R^3$ or $R^4$ are, for example any type of alkylcarbonyloxy or arylcarbonyloxy.

Carbamoyloxy substituents for $R^1$, $R^2$, $R^3$ or $R^4$ are, for example, any type of alkycarbamoyloxy or arylcarbamoyloxy.

Ureido substituents for $R^1$, $R^2$, $R^3$ or $R^4$ are, for example any type of alkylureido, arylureido or hetarylureido.

Sulphamoylamino substituents for $R^1$, $R^2$, $R^3$ or $R^4$ are, for example, any type of alkylsulphamoylamino or arylsulphamoylamino.

Heterocyclic substituents for $R^1$, $R^2$, $R^3$ or $R^4$ are preferably 5- to 7-membered ring heterocyclics; typical examples are 2-furyl, 2-thienyl, 2-pyrimidyl, 2-benzothiazolyl, 1-pyrrolyl, 1-tetrazoyl.

Heterocyclyloxy substituents for $R^1$, $R^2$, $R^3$ or $R^4$ are preferably 5- to 7-membered ring heterocyclics attached via an O atom; typical examples are 3,4,5,6-tetrahydropyranyl2-oxy, 1-phenyltetrazole-5-oxy.

Heterocyclylthio substituents for $R^1$, $R^2$, $R^3$ or $R^4$ are preferably 5- to 7-membered ring heterocyclics attached via an S atom; typical examples are 2-pyridylthio, 2-benzothiazolylthio, 2,4-diphenoxy-1,3,5-triazine-6-yl-thio.

Imido substituents for $R^1$, $R^2$, $R^3$ or $R^4$ are, for example, succinimido, 3-heptadecyisuccinimido, phthalimido, glutarimido.

Spiro substituents for $R^1$, $R^2$, $R^3$ or $R^4$ are, for example, spiro[3,3]heptan-1-yl.

Bridged hydrocarbon residues for $R^1$, $R^2$, $R^3$ or $R^4$ are for example, bicyclo[2,2,] heptan-1-yl, tricyclo[3,2,1,1]- decan-1-yl, 7,7 -dimethylbicyclo [2,2,1] heptany-1-yl.

A residue represented by X which may be eliminated under chromogenic development conditions may, for example, be: H, a halogen atom, such as Cl, Br or F, substituents such as: alkoxy, aryloxy, heterocyclyloxy, acyloxy, sulphonyloxy, alkoxycarbonyloxy, aryloxycarbonyloxy, alkyloxalyloxy, alkoxyoxalyloxy, alkyithio, arylthio, heterocyclylthio, alkyloxythiocarbonylthio, acylamino, sulphonamido, a heterocyclic containing nitrogen, which is attached to the coupler residue via an N atom, alkoxycarbonylamino, aryloxycarbonylamino, carboxyl, —N=N—aryl.

Depending upon the X substituent at the site capable of coupling, the cyan couplers according to the invention couple either in accordance with the 4-equivalent principle or as 2-equivalent couplers, wherein the eliminated nucieophilic residue may bring about specific photographic effects. A nucleophilic residue may moreover be eliminated which does not develop its photographic effect until after an intermediate member has been eliminated.

A group denoted by X in formula I and formula II which may be eliminated under chromogenic development conditions is, for example, either itself the residue of a photographically active compound or a group which, once eliminated from the coupling site of the coupler on coupling thereof with the silver halide developer oxidation product, is capable of releasing a residue of a photographically active compound attached thereto only in a subsequent reaction. Such a group is also described as a time control member, because in many cases there is a delay in the release of the residue of the photographically active compound attached thereto and this residue may only then become active. Known time control members are, for example, a group

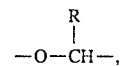

wherein the O atom is attached to the coupling site of the coupler and the C atom is attached to an N atom of a photographically active compound (for example DE-A-28 03 145), a group which, once eliminated from the coupler, undergoes an intramolecular nucleophilic displacement reaction, so releasing the photographically active compound (for example DE-A-28 55 697), a group in which, after elimination from the coupler, an electron transfer may occur along a conjugated system, so releasing the photographically active compound (for example DE-A 31 05 026), or a group

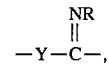

in which Y (for example —O—) is attached to the coupling site of the coupler and the C atom is attached to an atom of the photographically active compound and in which R may, for example, denote aryl (for example EP-A-0 127 063). The time control member may also be a group which, once eliminated from the coupling site of the coupler, may itself enter into a coupling reaction or a redox reaction and, as a consequence of such a reaction, release the photographically active compound attached thereto.

The group which may be eliminated under chromogenic development conditions is, for example, an organic group which is generally attached via an oxygen, sulphur or nitrogen atom to the coupling site of the coupler molecule. Should the eliminable group be a cyclic group, the attachment to the coupling site of the coupler molecule may be achieved either directly via an atom which is a constituent of a ring, for example a nitrogen atom, or indirectly via an intermediate binding link. Such eliminable groups are known in great numbers, for example as the fugitive groups of 2-equivalent couplers.

Examples of eliminable groups attached via oxygen are of the formula

in which $R^5$ denotes an acyclic or cyclic organic residue, for example alkyl, aryl, a heterocyclic group or acyl, which is, for example, derived from an organic carboxylic or sulphonic acid.

In particularly preferred eliminable groups of this type, $R^5$ means an optionally substituted phenyl group. Such groups are described, for example, in U.S. Pat. No. 3,408,194, DE-A-24 56 076.

Examples of eliminable groups attached via nitrogen are described in the following unexamined German applications (DE-A-):

20 57 941, 21 63 812, 22 13 461, 22 19 917, 22 61 361, 22 63 875, 23 18 807, 23 29 587, 23 44 155, 23 63 675, 24 33 812, 24 41 779, 24 42 703, 25 28 638, 25 28 860, 26 37 817, 28 18 373, 30 20 416.

These are without exception 5- or 6-membered heterocyclic rings which are attached to the coupling site of the coupler via a ring nitrogen atom. In many cases, the heterocyclic rings contain activating groups, for example carbonyl or sulphonyl groups or double bonds, adjacent to the nitrogen atom which effects the bond to the coupler molecule.

Examples of such residues which may be eliminated under chromogenic development conditions are given below.

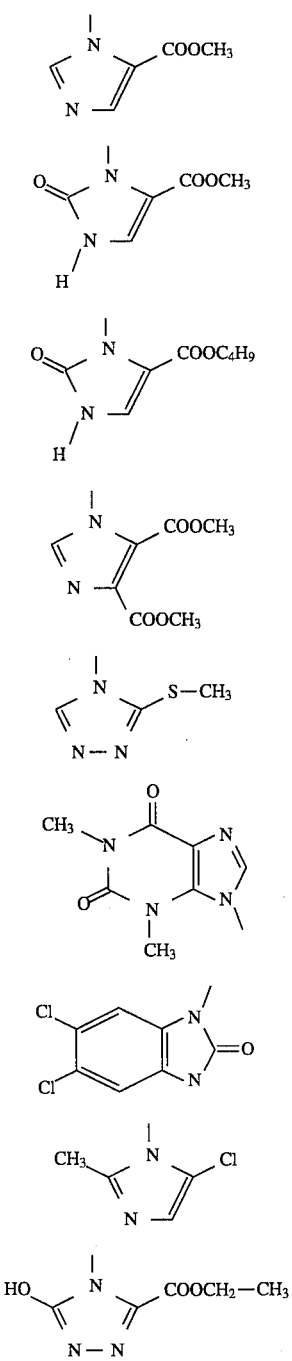

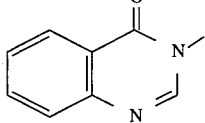

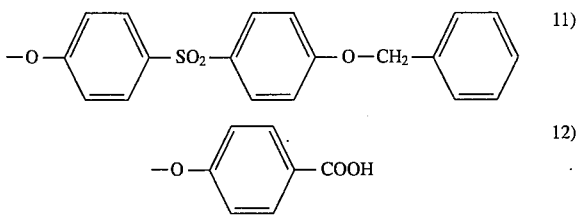

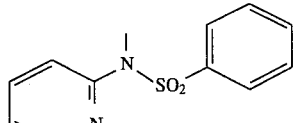

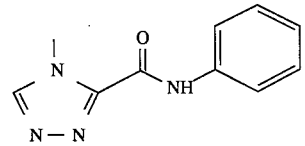

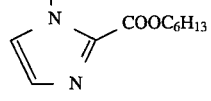

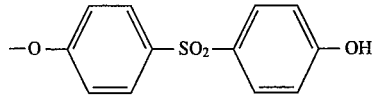

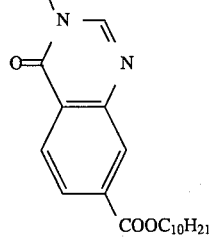

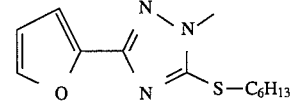

The photographically active compound may be a development inhibitor, a bleach inhibitor, a development accelerator, a "nucleating agent" which forms silver nuclei, a soluble mercaptan compound which promotes full development, a stabiliser, a whine coupler, a scavenger, an electron transfer agent, for example of the phenidone type, or a colour coupler compound.

Development inhibitors which may in particular be cited are those from the range of benzotriazoles, thienotriazoles, non-condensed monocyclic 1,2,3-triazoles, 3-alkylthio-1,2,4-triazoles, 5-mercapto-1-alkyl- or 5-mercapto-1-aryl-tetrazoles together with 2-mercapto-5-alkylthio-1,3,4-thiadiazoles.

The colour couplers according to the invention may moreover be provided with a ballast residue $R^1$, $R^2$, $R^3$, $R^4$. Ballast residues should be taken to be residues which enable or facilitate the non-diffusible inclusion of the colour couplers according to the invention in the hydrophilic colloids conventionally used in photographic materials. Suitable residues for this purpose are preferably organic residues, which generally contain linear or branched aliphatic groups and optionally also carbocyclic or heterocyclic aromatic groups generally having 8 to 20 C atoms.

Examples of colour couplers according to the invention are listed below.

| Coupler [Y—] | $R^3$ | X | Y | $R^5$ |
|---|---|---|---|---|
| 1 | H | Cl | —NH—CO— | —(CH$_2$)$_5$—O—[2,4-di-tert-pentylphenyl] |
| 2 | H | Br | —NH—CO— | —(CH$_2$)$_5$—O—[2,4-di-tert-pentylphenyl] |
| 3 | H | H | —NH—CO— | —(CH$_2$)$_5$—O—[2,4-di-tert-pentylphenyl] |
| 4 | —C$_{17}$H$_{35}$ | Cl | — | —H |
| 5 | —C$_{17}$H$_{35}$ | H | — | —H |
| 6 | H | Cl | —NH—CO— | —C$_{17}$H$_{35}$ |
| 7 | H | Cl | —NH—SO$_2$— | —C$_{17}$H$_{35}$ |
| 8 | H | Cl | —NH—SO$_2$— | —(CH$_2$)$_5$—O—[2,4-di-tert-pentylphenyl] |
| 9 | H | H | —NH—SO$_2$— | —(CH$_2$)$_5$—O—[2,4-di-tert-pentylphenyl] |
| 10 | H | H | —NH—SO$_2$— | —(CH$_2$)$_5$—O—[2-Cl-4,6-di-tert-pentylphenyl] |
| 11 | H | Cl | —NH—CO— | —CH(C$_4$H$_9$)—O—[2,4-di-tert-pentylphenyl] |

-continued
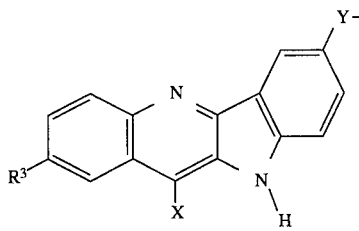
| Coupler [Y–] | R³ | X | Y | R⁵ |
|---|---|---|---|---|
| 12 | H | H | —NH—CO— | 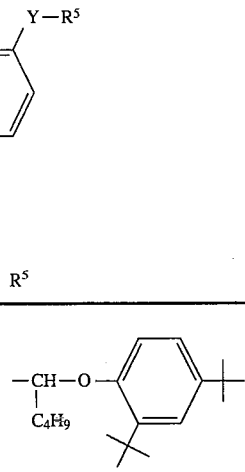 |
| 13 | H | Cl | —NH—CO— | 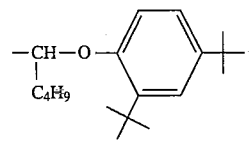 |
| 14 | H | Cl | —NH—CO— | 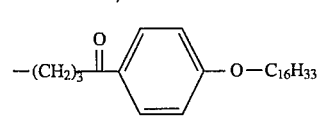 |
| 15 | H | Cl | —NH—SO$_2$— | 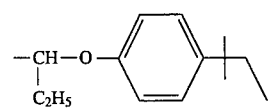 |
| 16 | H | Cl | —NH—CO— | 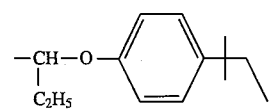 |
| 17 | H | H | —NH—CO— | 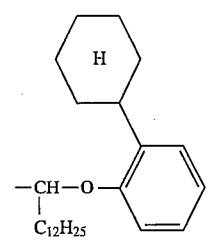 |
| 18 | H | Cl | —NH—SO$_2$— | 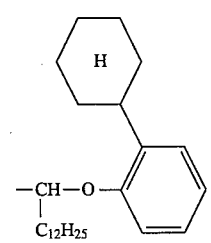 |
| 19 | H | Cl | —NH—CO— | 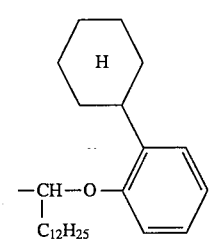 |

-continued
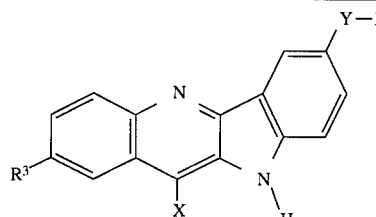
| Coupler [Y—] | R³ | X | Y | R⁵ |
|---|---|---|---|---|
| 20 | H | H | —NH—CO— | 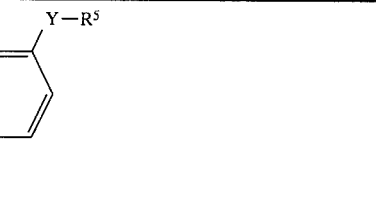 |
| 21 | H | Cl | —NH—CO— | 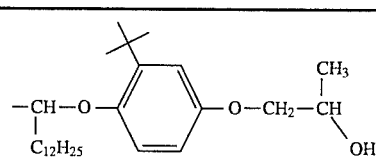 |
| 22 | H | Cl | —NH—CO— | 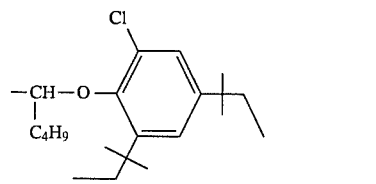 |
| 23 | H | H | —NH—CO— | 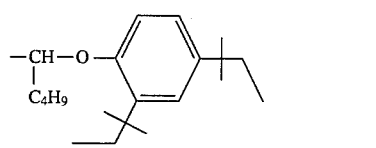 |
| 24 | H | H | —NH—CO— | 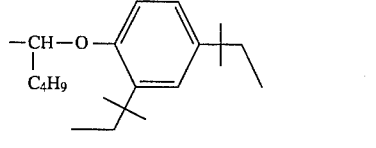 |
| 25 | H | Cl | —NH—CO— | 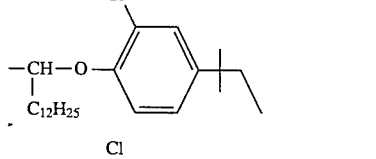 |
| 26 | H | Cl | —NH—CO— | 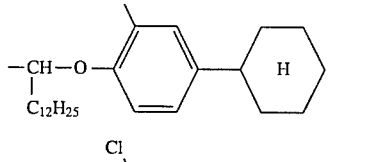 |
| 27 | H | Cl | —NH—CO— | 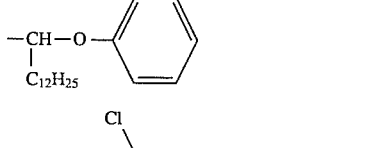 |
| 28 | H | Cl | —NH—CO— | 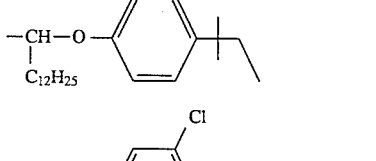 |

-continued
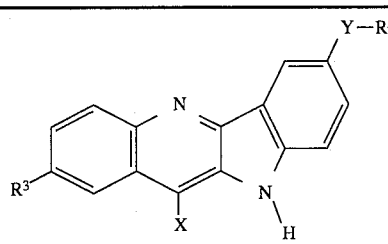
| Coupler [Y—] | R³ | X | Y | R⁵ |
|---|---|---|---|---|
| 29 | H | Cl | —NH—CO— | 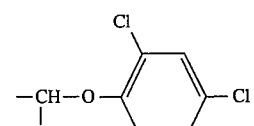 |
| 30 | H | H | —NH—CO— | 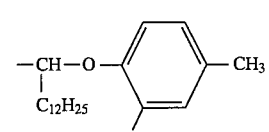 |
| 31 | H | Cl | —NH—CO— | 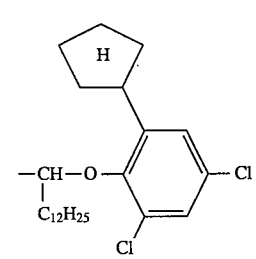 |
| 32 | H | Cl | —NH—CO— | 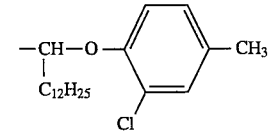 |
| 33 | H | Cl | —NH—CO— | 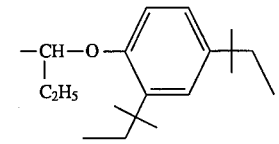 |
| 34 | H | Br | —NH—CO— | 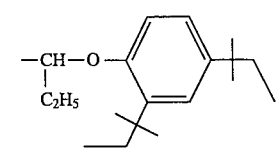 |
| 35 | H | H | —NH—CO— | 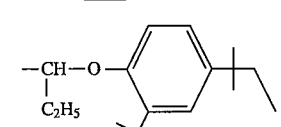 |
| 36 | H | —S—CH$_2$—CH(OH)—CH$_2$OH | —NH—CO— | 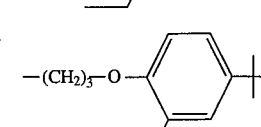 |

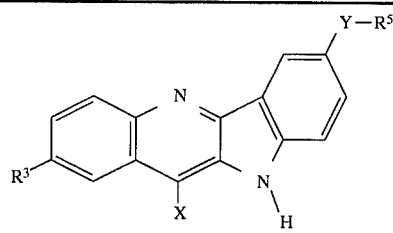

| Coupler [Y—] | R³ | X | Y | R⁵ |
|---|---|---|---|---|
| 37 | —H | —S—(tetrazole with N-Ph) | —NH—CO— | —(CH$_2$)$_5$—O—(2,4-di-tert-pentylphenyl) |
| 38 | —H | (1,2,3-triazol-yl)—S—CH(CH$_3$)—COOC$_5$H$_{11}$ | —NH—CO— | —CH(C$_4$H$_9$)—O—(2-Cl, 4,6-di-tert-pentylphenyl) |
| 39 | —H | —S—(CH$_2$)$_2$—COOH | —NH—CO— | —(CH$_2$)$_5$—O—(2,4-di-tert-pentylphenyl) |
| 40 | —H | —S—(CH$_2$)$_2$—COOH | —NH—CO— | —CH(C$_2$H$_5$)—O—(2,4-di-tert-pentylphenyl) |
| 41 | —H | —S—(4-phenylthiazol-2-yl) | —NH—CO— | —CH(C$_{12}$H$_{25}$)—O—(2-CN-phenyl) |

Indoloquinolines are organic compounds which have been infrequently described (in particular in derivatised form as a class of substances with anti-tumour potential), but have not been described as photographic coupling components to produce yellow dye chromophores.

The colour couplers according to the invention may be produced inter alia in accordance with the following general principle:

Cyclisation of 4-hydroxyquinolines or the tautomeric 4-quinolinones thereof with anilines in polyphosphoric acid to yield 5H,10H-indolo-[3,2-b] quinolin-11-onene, which with phosphorus oxytrihalide give rise to the 11-halogenoindolo[3,2-b]quinolines. The latter may then be further electrophilically substituted or also dehalogenated or be exchanged for substituents X in position 11. Electrophilic substitution in the form of nitration, for example, yields after reduction 7-amino derivatives, which then result in colour couplers ballasted with "ballast residue acid chlorides", which facilitate their non-diffusible inclusion in photographic materials.

Synthesis may, for example, proceed in accordance with the following general scheme.

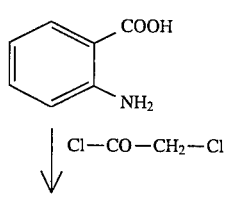

-continued

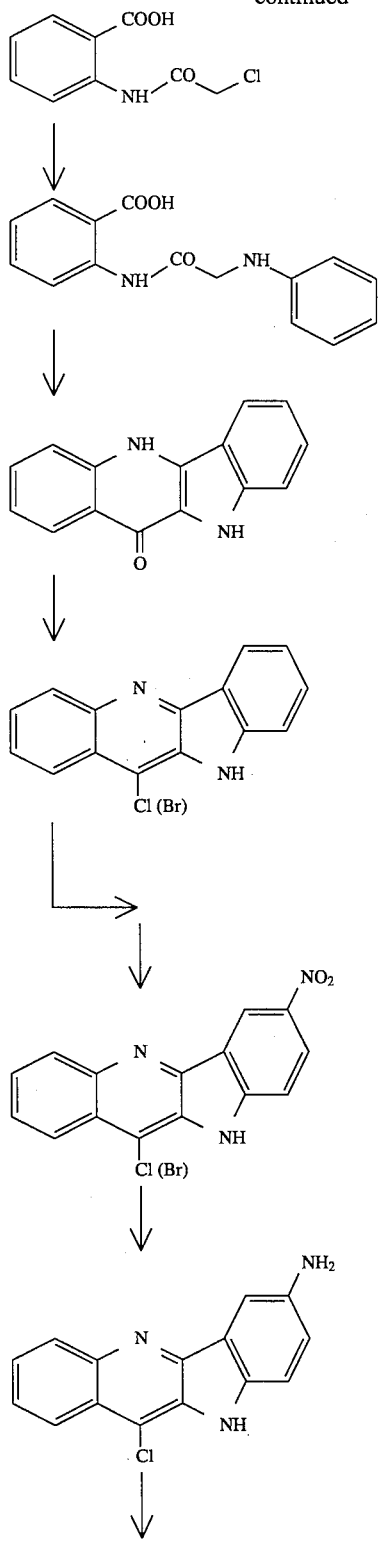

-continued

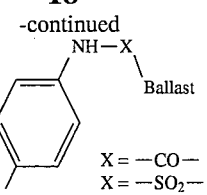

X = —CO—
X = —SO₂—

In the process according to the invention, a colour photographic material which contains at least one silver halide emulsion exposed in accordance with an image is developed with a colour developer compound of the p-phenylenediamine type. The colour couplers according to the invention may here be contained in the material in spatial and spectral association with a photosensitive silver halide emulsion layer.

A spatial association should here be taken to mean that the colour coupler is arranged spatially in relation to the silver halide emulsion layer in such a manner that it is possible for them to interact, so permitting the silver image formed on development no be congruent with the colour image produced from the colour coupler. This is generally achieved by the colour coupler's being contained in the silver halide layer itself or in an adjacent, optionally non-photosensitive, binder layer.

A spectral association should be taken to mean that there is a certain relationship between the spectral sensitivity of the photosensitive silver halide emulsion layer concerned and the colour of the partial colour image produced from the spatially associated colour coupler, wherein each of the spectral sensitivities (red, green, blue) is associated with a different colour of the partial colour image concerned (for example cyan, magenta, yellow). In accordance with the colour (yellow) formed from the colour couplers according to the invention, these couplers are preferably associated with a silver halide emulsion layer for blue light.

The material may furthermore contain compounds other than couplers, which may, for example, liberate a development inhibitor, a development accelerator, a bleach accelerator, a developer, a silver halide solvent, a fogging agent or an anti-fogging agent, for example so-called DIR hydroquinones and other compounds as are, for example, described in U.S. Pat. No. 4,636,546, 4,345,024, 4,684,604 and in DE-A-31 45 640, 25 15 213, 24 47 079 and in EP-A-198 438. These compounds fulfil the same function as the DIR, DAR or FAR couplers, except that they form no coupling products.

High molecular weight colour couplers are, for example, described in DE-C-1 297 417, DE-A-24 07 569, DE-A-31 48 125, DE-A-32 17 200, DE-A-33 20 079 DE-A-33 24 932, DE-A-33 31 743, DE-A-33 40 376, EP-A-27 284, U.S. Pat. No. 4,080,211. The high-molecular weight colour couplers are generally produced by polymerisation of ethytenically unsaturated monomeric colour couplers. They may, however, also be obtained by polyaddition or polycondensation.

The incorporation of the colour couplers according to the invention into the silver halide emulsion layers may proceed by initially producing a solution, dispersion or emulsion of the compound concerned and then adding it to the pouring solution for the layer concerned. Selection of the appropriate solvent or dispersant depends on the particular solubility of the compound.

Methods for the introduction of compounds which are substantially insoluble in water by a grinding process are described, for example, in DE-A-26 09 741 and DE-A-26 09 742.

Hydrophobic compounds may also be introduced into the pouring solution by using high-boiling solvents, so-called oil formers. Corresponding methods are described, for example, in U.S. Pat. No. 2,322,027, U.S. Pat. No. 2,801, 170, and EP-A-0 043 037.

Oligomers or polymers, so-called polymeric oil formers, may be used instead of high-boiling solvents.

The compounds may also be introduced into the pouring solution in the form of filled latices. Reference is, for example, made to DE-A-25 41 230, DE-A-25 41 274, DE-A-28 35 856, EP-A-0 014 921, EP-A-0 069 671, EP-A-0 130 115, U.S. Pat. No. 4,291,113.

The non-diffusible inclusion of anionic water-soluble compounds (for example of dyes) may also proceed with the assistance of cationic polymers, so-called mordanting polymers.

Suitable oil formers are, for example, phthalic acid alkyl esters, phosphonic acid esters, phosphoric acid esters, citric acid esters, benzoic acid esters, amides, fatty acid esters, trimesic acid esters, alcohols, phenols, aniline derivatives and hydrocarbons.

Examples of suitable oil formers are dibutyl phthalate, dicyclohexyl phthalate, di-2-ethylhexyl phthalate, decyl phthalate, triphenyl phosphate, tricresyl phosphate, 2-ethylhexyldiphenyl phosphate, tricyclohexyl phosphate, tri-2-ethylhexyl phosphate, tridecyl phosphate, tributoxyethyl phosphate, trichloropropyl phosphate, di-2-ethylhexyl phenyl phosphate, 2-ethylhexyl benzoate, dodecyl benzoate, 2-ethylhexyl-p-hydroxybenzoate, diethyldodecanamide, N-tetradecylpyrrolidone, isostearyl alcohol, 2,4-di-t-amyl alcohol, dioctyl acetate, glycerol tributyrate, iso-stearyl lactate, trioctyl citrate, N,N-dibutyl-2-butoxy-5-t-octyl aniline, paraffin, dodecylbenzene and diisopropylnaphthalene.

Colour photographic negative materials are conventionally processed by developing, bleaching, fixing and rinsing or by developing, bleaching, fixing and stabilising without subsequent rinsing, wherein bleaching and fixing may be combined into a single processing stage. Colour developer compounds which may be used are all developer compounds having the ability to react, in the form of their oxidation product, with colour couplers to yield azomethine dyes. Suitable colour developer compounds are aromatic compounds containing at least one primary amino group of the p-phenylenediamine type, for example N,N-dialkyl-p-pheneylenediamines such as N,N-diethyl-p-phenylenediamine, 1-(N-ethyl-N-methanesulphonamidoethyl)-3-methyl-p-phenylenediamine, 1-(N-ethyl-N-hydroxyethyl)-3-methyl-p-phenylenediamine and 1-(N-ethyl-N-methoxyethyl)-3-methyl- p-phenylenediamine. Further usable colour developers are described, for example, in J. Amer. Chem. Soc 73, 3106 (1951) and G. Haist, Modern Photographic Processing, 1979, John Wiley & Sons, New York, page 545 et seq..

Provided that the colour couplers according to the invention are alkali-soluble compounds, they may also be added to the colour developer (instead of to the photographic material).

Colour development may be followed by an acidic stop bath or rinsing.

Conventionally, the material is bleached and fixed immediately after colour development. Bleaches which may be used are, for example, Fe(III) salts and Fe(III) complex salts such as ferricyanides, dichromates, water soluble cobalt complexes. Iron(III) complexes of aminopolycarboxylic acids are particularly preferred, in particular for example complexes of ethylenediaminetetraacetic acid, propylenediaminetetraacetic acid, diethylenetriaminepentaacetic acid, nitrilotriacetic acid, iminodiacetic acid, N-hydroxyethylethylenediaminetriacetic acid, alkyliminodicarboxylic acid and of corresponding phosphonic acids. Persulphates and peroxides, for example hydrogen peroxide, are also suitable as bleaches.

The bleaching-fixing bath or fixing bath is usually followed by rinsing, which is performed as countercurrent rinsing or comprises several tanks with their own water supply.

Favourable results may be obtained by using a subsequent finishing bath which contains little or no formaldehyde.

Rinsing may, however, be completely replaced with a stabilising bath, which is conventionally operated countercurrently. If formaldehyde is added, this stabilising bath also assumes the function of a finishing bath.

In colour reversal materials, development first proceeds with a black-&-white developer, the oxidation product of which is not capable of reacting with the colour coupler. This is followed by a diffuse second exposure and then development with a colour developer, bleaching and fixing.

EXAMPLE

Individual yellow cast structures are prepared for a colour photographic material suitable for rapid processing by applying, in each case, 4 layers in the stated sequence onto one side of a film base made from paper laminated on both sides with polyethylene.

The stated weights relate in each case to 1 m$^2$.

The corresponding quantities of AgNO$_3$ are stated for the applied quantity of silver halide.

Test material 1A (comparison)

Layer 1; Substrate layer with 0.2 g of gelatine
Layer 2% Blue-sensitive silver halide emulsion layer (99.5 mol.% AgCl and 0.5 mol.% AgBr, average grain diameter 0.8 μm) prepared from
  0.46 g of AgNO$_3$
  1.3 g of gelatine
  0.5 g of yellow coupler XY-1
  0.2 g of white coupler XW-1
  0.5 g of polyester prepared from adipic acid,
  1,3-butanediol and 1,6-hexanediol
Layer 3:
  1.1 g of gelatine
  0.06 g of dioctylhydroquinone
  0.06 g of di-n-butyl phthalate
Layer 4:
  0.9 g of gelatine
  0.3 g of instant hardener XH-1

The following compounds were used in test material 1A.

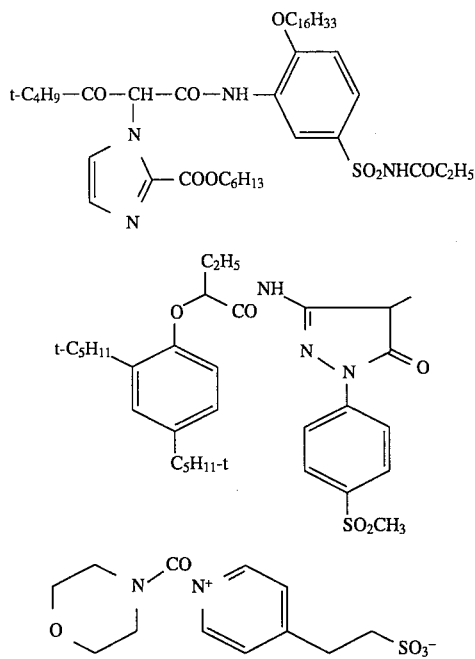

Test material 1B (according to the invention)

As-test material 1A, but with the following change:

Layer 2 contains 0.58 g of coupler Y-1 according to the invention instead of comparison coupler XY-1.

The resultant test materials were exposed behind a grey wedge with blue light and processed as stated below.

| a) Colour development 45 s | 35° C. |
|---|---|
| Triethanolamine | 9.0 g |
| N,N-diethylhydroxylamine | 6.0 g |
| Diethylene glycol | 0.05 g |
| 3-methyl-4-amino-N-ethyl-N-methane-sulphonamidoethyl-aniline sulphate | 6.0 g |
| Potassium sulphate | 0.2 g |
| Triethylene glycol | 0.05 g |
| Potassium carbonate | 22.0 g |
| Potassium hydroxide | 0.4 g |
| Ethylenediaminetetraacetic acid | 2.2 g |
| make up to 1,000 ml with water; pH 9.2 | |
| b) Bleaching/fixing bath, 45 s | 35° C. |
| Ammonium thiosulphate | 75.0 g |
| Sodium hydrogen sulphite | 13.5 g |
| Ammonium acetate | 2.0 g |
| Ethylenediaminetetraacetic acid (iron-ammonium salt) | 57.0 g |
| 25 wt. % ammonia | 9.5 g |
| Acetic acid | 9.0 g |
| make up to 1,000 ml with water; pH 5.5 | |
| c) Rinsing, 2 min | 33° C. |

A yellow coloured wedge is obtained in each case for both layer structure 1A (comparison) and layer structure 1B (invention). The maximum densities are 2.2 and 2.08 respectively measured through a blue filter. The coloured wedge obtained with the material according to the invention is distinguished by elevated colour purity or brightness.

This example proves that the compounds according to the invention are suitable as colour couplers.

I claim:

1. A photographic color development process comprising exposing a color photographic recording material having at least one silver halide emulsion layer with an image, developing in the presence of a color coupler compound and a color developer compound, wherein the color coupler compound is of the formula I

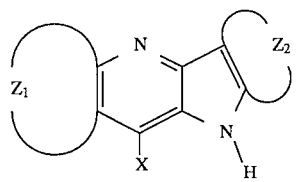

in which:

$Z_1$ and $Z_2$ are the same or different and mean residues to complete 5-, 6- or 7-membered aromatic or heteroaromatic rings; these rings substituted with substituents $R^1$, $R^2$, $R^3$ and R4;

$R^1$, $R^2$, $R^3$ and $R^4$ are identical or different and are a hydrogen atom or a substituent;

X means H or a substituent which is released under chromogenic development conditions.

2. The photographic color development process according to claim 1, wherein the color coupler compound is of the formula II

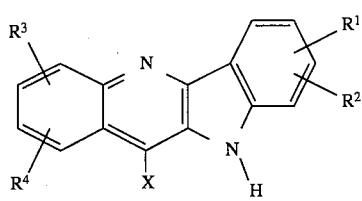

in which:

$R_1$, $R^2$, $R^3$ and $R^4$ are the same or different and mean an H atom or a substituent;

X means an H atom or a residue which is eliminated under chromogenic development conditions.

3. A color photographic recording material comprising a film base and at least one photosensitive silver halide emulsion layer arranged thereon, wherein said at least one photosensitive silver halide emulsion layer is associated with a color coupler, in that the color coupler is of the formula II in which:

$R^1$, $R^2$, $R^3$ and $R^4$ are the same or different an mean an H atom or a substituent;

X means an H atom or a residue which is eliminated under chromogenic development conditions.

4. The recording material according to claim 3, wherein the color coupler is of the formula III

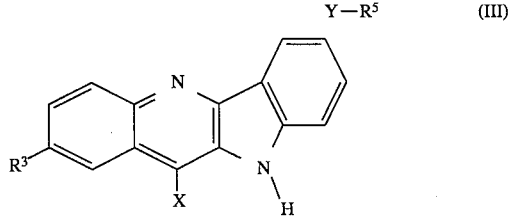

in which $R_3$ means H or alkyl;

$R_5$ means an optionally substituted alkyl group;

X means H or a residue which may be eliminated under chromogenic development conditions;

Y means —NH—CO— or NH—$SO_2$.

5. The photographic color development process according to claim 1, wherein the substituents $R^1$, $R^2$, $R^3$, and $R^4$ are identical or different and are halogen, alkyl, cycloalkyl, aryl, anilino, acylamino, sulphonamido, alkylthio, arylthio, alkenyl, cycloalkenyl, alkynyl, heterocyclyl, sulphonyl, sulphinyl, phosphonyl, acyl, carbamoyl, sulphamoyl, cyano, alkoxy, sulphonyloxy, aryloxy, heterocyclyloxy, siloxy, acyloxy, carbamoyloxy, amino, alkylamino, imido, ureido, sulphamoylamino, alkoxycarbonylamino, aryloxycarbonylamino, alkoxycarbonyl, aryloxycarbonyl, heterocyclylthio, thioureido, carboxy, nitro, sulphonate, spiro substituents or bridged hydrocarbon residues.

6. The photographic color development process according to claim 1, wherein $R^3$ is hydrogen or $-C_{17}H_{35}$.

7. The photographic color development process according to claim 1, wherein X is Cl, Br, H or $-S-(CH_2)_2-COOH$.

8. The photographic color development process according to claim 6, wherein X is Cl, Br, H or $-S-(CH_2)_2-COOH$.

9. The photographic color development process according to claim 1, wherein Y is $-NH-CO-$ or $-NH-SO_2$.

10. The photographic color development process according to claim 8, wherein Y is $-NH-CO-$ or $-NH-SO_2$.

* * * * *